(12) United States Patent
Sexton et al.

(10) Patent No.: US 7,461,655 B2
(45) Date of Patent: Dec. 9, 2008

(54) PORTABLE INHALER WITH TEMPERATURE CONTROL

(75) Inventors: Douglas A. Sexton, La Jolla, CA (US); Winthrop D. Childers, San Diego, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 585 days.

(21) Appl. No.: 11/209,576

(22) Filed: Aug. 23, 2005

(65) Prior Publication Data

US 2007/0062523 A1 Mar. 22, 2007

(51) Int. Cl.
*A61M 16/00* (2006.01)
*A61M 15/00* (2006.01)
*A62B 7/00* (2006.01)

(52) U.S. Cl. ............... 128/204.15; 128/204.17; 128/203.26; 128/203.27; 128/200.11; 128/203.12

(58) Field of Classification Search ............ 128/203.26, 128/203.27, 204.15, 204.17, 204.18, 204.21, 128/204.22, 204.29
See application file for complete search history.

(56) References Cited

U.S. PATENT DOCUMENTS

| | | | |
|---|---|---|---|
| 4,399,349 A | 8/1983 | Deming et al. | |
| 5,242,403 A * | 9/1993 | Falb et al. ............... | 604/113 |
| 5,889,684 A | 3/1999 | Ben-David et al. | |
| 6,158,431 A | 12/2000 | Poole | |
| 6,637,430 B1 * | 10/2003 | Voges et al. ............. | 128/200.14 |
| 6,684,880 B2 * | 2/2004 | Trueba .................... | 128/200.16 |
| 6,691,058 B2 * | 2/2004 | Blakley .................. | 702/130 |
| 6,772,756 B2 * | 8/2004 | Shayan ................... | 128/203.26 |
| 6,799,572 B2 * | 10/2004 | Nichols et al. .......... | 128/203.26 |
| 7,225,807 B2 * | 6/2007 | Papania et al. .......... | 128/203.12 |
| 2003/0101991 A1 * | 6/2003 | Trueba .................... | 128/200.14 |
| 2004/0134494 A1 | 7/2004 | Papania et al. | |
| 2004/0211418 A1 | 10/2004 | Shayan | |

* cited by examiner

*Primary Examiner*—Justine R Yu
*Assistant Examiner*—Clinton Ostrup

(57) ABSTRACT

An inhaler operable to control a temperature of a medicament of the inhaler includes a medicament reservoir being configured to store a medicament therein. A medicament ejector is operably coupled to the medicament reservoir and is configured to eject the medicament from the reservoir to deliver the medicament to a patient. A controllable thermal source is in thermal communication with at least an inside portion of the medicament reservoir and is operable to controllably affect a temperature of the medicament. A thermal control system is in operable communication with the controllable thermal source and is configured to control the thermal source to maintain the medicament within a predetermined temperature range.

27 Claims, 2 Drawing Sheets

PORTABLE INHALER WITH TEMPERATURE CONTROL

FIELD OF THE INVENTION

The present invention relates generally to systems for controlling the temperature of medicaments stored in a portable or hand-held drug delivery device.

BACKGROUND OF THE INVENTION

Many medicinal inhalants have temperature-dependent shelf lives that dictate that the medicaments be stored at a particular temperature to maintain a usable life of the medicament. Examples of commonly used medicaments having temperature-dependent shelf lives include insulin, interferon, etc. In an institutional setting, such as a home or medical treatment facility, these types of medicaments can be stored in appliances such as refrigerators with little trouble. However, problems arise when a patient attempts to store or travel with the medicament in environments having temperatures above or below the recommended storage temperature of the medicinal inhalant.

Thus, while many patients should carry such medicaments with them throughout the day, removing the medicaments from a controlled storage environment, such as a refrigerator, can result in the medicaments prematurely expiring. This can serve to deter patients from carrying such medicaments with them, or can result in a patient's medicament expiring prematurely without patient knowledge.

Several systems have been developed in an effort to provide portability to inhalants having limited, temperature-dependent shelf lives. One known method includes providing medicament inhalers having medicament in a dry powder form that can be mixed with a fluid prior to dispensing the medicament to the patient. As the medicament is stored within the inhaler in a dry form, the shelf life of the medicament is not as temperature-dependent as if stored in a liquid form. While this solution has met with some success, the requirement of mixing the powder with a liquid prior to administering the inhalant to a patient has necessitated the use of relatively sophisticated internal mixing systems which result in inhalers that may be inconvenient, unreliable and overly complex. Also, some types of medicines are not well suited to be reduced to powdered form.

Another attempt to address these problems has been by providing cold packs that are placed adjacent a reservoir of medicament in drug delivery systems in an attempt to cool the medicament stored in the reservoir. This system has proved problematic in that the medicament can become overly warm without the user become aware of this fact when the cold packs lose their cooling capacity during use. This system is also very dependent on the outside environment, as a very hot environment can result in the cold packs losing their cooling capacity more quickly than in a cooler environment. Also, such systems are not generally capable of controllably cooling a medicament in a reservoir to a variable range of temperatures, but will rather only lower a temperature of a medicament to some equilibrium temperature dependent on the cooling capacity of the cold packs, the size of the medicament reservoir, etc.

Accordingly, while many patients can benefit from a system that provides portability to temperature-dependent inhalants, current solutions to this problem have proven ineffective for a variety of reasons.

DETAILED DESCRIPTION OF THE PREFERRED EMBODIMENT(S)

Figure 1:
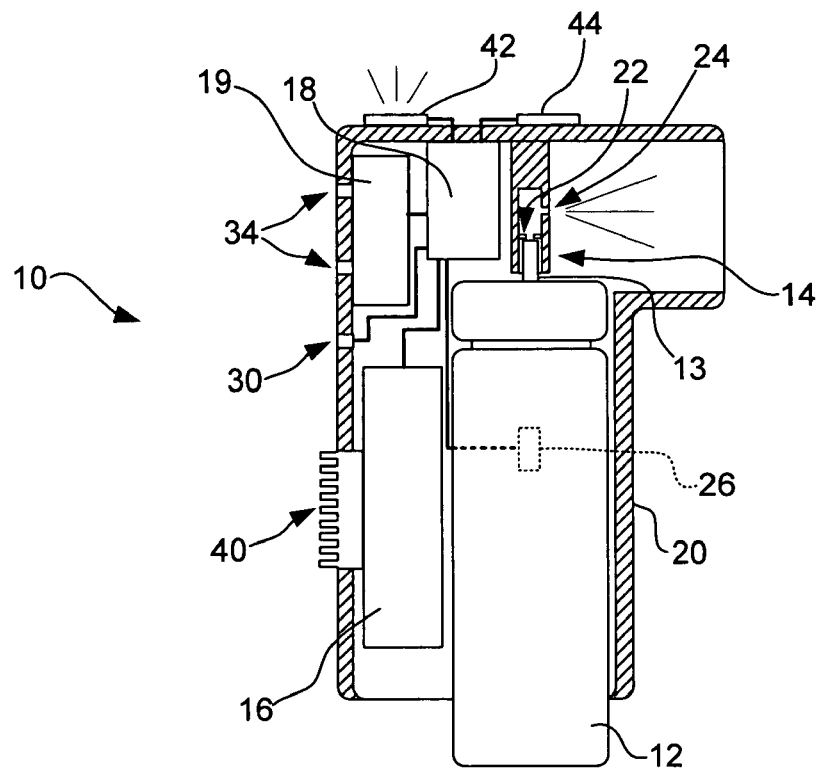
FIG. 1 is a schematic view of an inhaler in accordance with an embodiment of the present invention.

Before particular embodiments of the present invention are disclosed and described, it is to be understood that this invention is not limited to the particular process and materials disclosed herein as such may vary to some degree. It is also to be understood that the terminology used herein is used for the purpose of describing particular embodiments only and is not intended to be limiting, as the scope of the present invention will be defined only by the appended claims and equivalents thereof.

In describing and claiming the present invention, the following terminology will be used:

The singular forms "a," "an," and "the" include plural referents unless the context clearly dictates otherwise.

As used herein, the term "medicament" is to be understood to refer to a variety of types of pharmacological materials intended for application or delivery to any of a variety of patients, either human or otherwise, through a variety of delivery mechanisms. While not so required, in one aspect of the invention, the medicament is a pharmacological material intended for delivery to the patient by inhalation.

As used herein, the term "controllable thermal source" is to be understood to refer to a controllable device or system capable of removing or adding thermal energy (e.g., heat) to another device or system. Examples of controllable thermal sources include refrigeration systems, heating systems, etc., that are controlled by way of adjustable set-points, etc. For purposes of the present discussion, a thermal source that is not capable of being controlled, such as a volume of frozen water or other frozen aqueous composition, is not considered a controllable thermal source.

As used herein, the term "thermal communication" is to be understood to refer to a relationship between two or more devices or systems wherein heat can flow between the two or more devices or systems. For example, two devices can be in thermal communication due to the fact that they are in contact with one another, or due to the fact that they are of sufficiently close proximity that heat can flow from one device to another.

As used herein, the term "chargeable power source" is to be understood to refer to a power source with a finite charge or energy capacity that can be restored by a charging system after some level of discharging has occurred.

It is to be understood that the various features shown in the attached figures are for the purposes of illustration and do not in any manner limit the present invention. In particular, various components of the invention are shown schematically and are not to be construed to limit the invention to any particular size or shape of such components, nor are sizes and/or shapes of components relative to one another intended to limit one or another of the components.

It has been recognized that it would be advantageous to develop a system that provides for controlled cooling of a medicament while the medicament is stored in an inhaler in a use-ready state. The present invention provides an inhaler operable to control a temperature of a medicament of the inhaler, including a medicament reservoir configured to store a medicament therein. A medicament ejector can be operably coupled to the medicament reservoir and can be configured to eject the medicament from the reservoir to deliver the medicament to a patient. A controllable thermal source can be in thermal communication with at least an inside portion of the medicament reservoir and can be operable to controllably affect a temperature of the medicament. A thermal control system can be in operable communication with the controllable thermal source and can be configured to control the thermal source to maintain the medicament within a predetermined temperature range.

In accordance with another aspect of the invention, an inhaler operable to control a temperature of a medicament stored on or in the inhaler is provided, including means for storing a medicament on or in the inhaler, means for ejecting the medicament from the inhaler to deliver the medicament to a patient, means for affecting a temperature of the medicament, and means for controlling the means for affecting the temperature of the medicament to enable control of the temperature of the medicament within a predetermined temperature range.

In accordance with another aspect of the invention, a method for maintaining a medicament within a predetermined temperature range while the medicament is operably associated with an inhaler is provided, including the steps of: disposing a quantity of the medicament within a reservoir associated with the inhaler; affecting a temperature of the medicament with a thermal source; monitoring a temperature of the medicament; and controlling the thermal source to maintain the medicament within the predetermined temperature range.

Additional features and advantages of the invention will be apparent from the detailed description which follows, taken in conjunction with the accompanying drawings, which together illustrate, by way of example, features of the invention. As such, reference will now be made to the exemplary embodiments illustrated in the drawings, and specific language will be used herein to describe the same. It will nevertheless be understood that no limitation of the scope of the invention is thereby intended. Alterations and further modifications of the inventive features illustrated herein, and additional applications of the principles of the inventions as illustrated herein, which would occur to one skilled in the relevant art and having possession of this disclosure, are to be considered within the scope of the invention.

The present invention provides systems for storing medicament within or on a portable or hand-held inhaler while maintaining a temperature of the medicament within a temperature range recommended for storage of the medicament. Inhalers in accordance with the present invention can be used with a variety of medicaments and are particularly well suited for use with medicaments that have temperature-dependent shelf lives. An exemplary configuration of an inhaler in accordance with the present invention is shown generally at 10 in FIG. 1. The inhaler can be operable to control a temperature of a medicament of the inhaler, and can include a medicament reservoir 12 that can be configured to store a medicament (not shown) therein. A medicament ejector 14 can be operably coupled to the medicament reservoir and can be configured to eject the medicament from the reservoir to deliver the medicament to a patient (not shown). A controllable thermal source 16 can be in thermal communication with at least an inside portion of the medicament reservoir and can be operable to controllably affect a temperature of the medicament.

A thermal control system (in the embodiment shown the thermal control system is integrated with control system 18) can be in operable communication with the controllable thermal source 16 and can be configured to control the thermal source to maintain the medicament within a predetermined temperature range. A power source 19 can be coupled to the inhaler and can be operably coupled to the controllable thermal source and control system 18 to power the controllable thermal source and control system.

The reservoir 12 illustrated in FIG. 1 is representative of a reservoir of many conventional meter-dosed inhaler inserts in which actuation of an upper tubular tang 13 of the insert delivers a metered dose of medicament stored within the reservoir. Similar to conventional inhalers, as the reservoir is moved upwardly into body 20 of the present inhaler 10, tang 13 comes to rests against protrusions 22 formed within the inhaler. If the reservoir is forced upwardly beyond this point, the tubular tang is depressed toward reservoir 12 until a meter dose of medicament is expelled from the reservoir through the tubular tang (by propellant means well know in the art) and the medicament is ejected out of orifice 24 and delivered to the patient.

The present invention is suitable for use with other types of inhalers that utilize other means of ejecting powder or droplets including those that utilize electronically activated ejector heads that generate an aerosol. One example of these types of inhalers is an inhaler that utilizes mechanical vibration of a micro-perforated membrane to generate an aerosol. Another example utilizes an array of "bubble-jet" transducers that each creates droplets in response to a current pulse through a resistor. Another example utilizes an array of piezo-jet transducers that each generates droplets through the action of a piezoelectrically activated micromechanical device. Yet another example utilizes electrostatic forces near the tips of sharp conductors to form airborne droplets. The present invention complements inhalation devices utilizing a wide variety of drop ejectors that rely on thermal, mechanical, pressure, electrostatic, or other means to form droplets.

The present invention is suitable for use with conventional inhaler inserts. In addition, the present invention can be configured to include a stand-alone reservoir (not shown) that can be refilled with a medicament when depleted. Without regard to the type of reservoir utilized, the controllable thermal source 16 can be in thermal communication with at least an internal portion of the reservoir to affect a temperature of the medicament within the reservoir. In the embodiment shown in FIG. 1, the controllable thermal source is coupled within the body 20 of the inhaler 10 such that the reservoir 12 comes into thermal communication with the thermal source when the reservoir is inserted within the inhaler. As the thermal source cools or heats the reservoir, the medicament within the reservoir experiences a corresponding increase or decrease in temperature.

The thermal source 16 can be of a variety of types known to those of ordinary skill in the art, including thermoelectric devices designed to either heat or cool other devices or systems, or to alternately heat and cool other devices or systems. Cooling fins 40 can be operably coupled to the thermal source to direct heat produced by the thermal source away from the internal portions of the inhaler and the reservoir. In the embodiment shown in FIG. 1, the thermal source is controlled by a thermal control system portion of control system 18 that can include a variety of features found in conventional thermal control systems. For example, the thermal control system can include a processor (not shown) coupled with a data storage device (not shown) that allows an operator to input a specified temperature range set point in which the reservoir 12 is desired to be maintained.

A thermocouple 26 can be disposed adjacent a side of the reservoir 12 to monitor a temperature of at least an external portion of the reservoir. As the thermal control system detects that the reservoir has increased or decreased in temperature above or below the specified temperature range, the thermal source can be activated until the reservoir temperature is again within the specified range, at which point the thermal source can be deactivated. This process can continue in a closed-loop fashion to maintain the medicament in the reservoir within the desired temperature range to ensure the medicament exhibits a suitable shelf life.

While thermocouple 26 is shown in FIG. 1 as disposed adjacent an external side of the reservoir 12, it is to be understood that the thermocouple can be disposed in a variety of areas in or about the reservoir. The thermal control system portion of control system 18 can be designed to accommodate differing positions of the thermocouple relative to the medicament. For example, in the case where the thermocouple is disposed adjacent an outside portion of the reservoir, the thermal control system can be configured to maintain the external portion of the reservoir at a lower temperature than is desired to maintain the medicament within the reservoir, with the understanding that the internal portions of the reservoir will likely be at higher temperatures than external portions at any given time (assuming that the reservoir is cooled from a source external to the reservoir).

Figure 2:
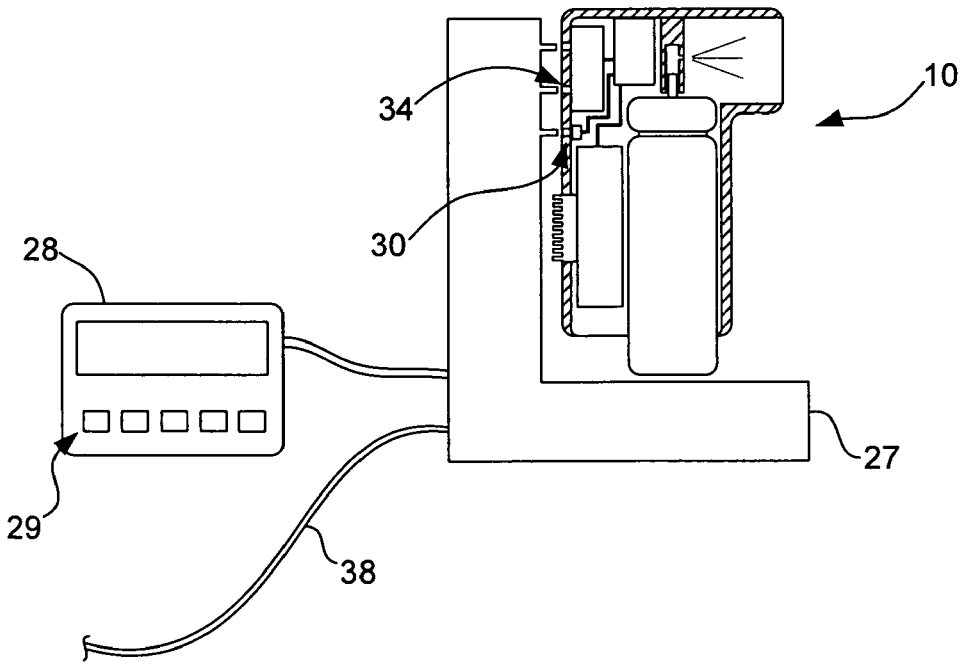
FIG. 2 is a schematic view of the inhaler of FIG. 1 in communication with a charging and controlling base unit in accordance with an embodiment of the present invention.

In addition to including the thermal control system, the control system 18 can also include circuitry that enables the inhaler 10 to be programmed for a variety of different types of medicaments and for a variety of different types of usage. For example, in the embodiment illustrated in FIG. 2, the inhaler system includes a base docking unit 27 that enables the control system to be programmed via a user interface 28. In this aspect of the invention, the inhaler 10 can be docked to the base unit and communication between the user interface and the control system can be achieved through data port 30, which can be, for example a USB data port. In this manner, the inhaler can be programmed to ensure that control parameters are correctly established for the type of medicament stored in the inhaler, the patient with which the inhaler will be used, the type of environment in which the inhaler will be carried or stored, etc.

The user interface 28 can be of a type known to those of ordinary skill in the art, and can include input keys 29 that allow an operator or user to program the control system 18 with various parameters. In addition to utilizing the user interface for this process, it is contemplated that the present inhaler can be programmed utilizing input devices (not shown) disposed on the inhaler to allow direct programming of the inhaler. Such input devices are well known to those of ordinary skill in the art.

The power source 19 utilized with the inhaler can be of a variety of known types, including, for example, batteries having a finite capacitance that can be recharged when partially or fully depleted. Recharging of the batteries can be accomplished via the base docking station 27, through ports or plugs 34. Conventional, alkaline batteries that are not normally rechargeable can also be utilized as the power source. By utilizing an "on-board" power source the present inhaler can be made portable, such that the inhaler can be carried on the person of a patient while the patient goes about his or her day, while maintaining the medicament stored in the inhaler within a desired temperature range.

The docking station 27 can include a power cord 38 that can be coupled with an external power source to facilitate charging of the on-board power source 19. For example, the power cord can be coupled to a conventional, 120-volt outlet to thereby charge the power source and also, if desired, to power the user interface 28 and the inhaler 10 while programming the inhaler. In addition, the power cord can be coupled to a 12-volt power source of an automobile or other vehicle to power the recharging process or the programming process. The system can be adapted to be powered by a variety of known power sources external to the system, as would occur to one having ordinary skill in the art.

The inhaler 10 can also include a monitoring system (shown integrated with control system 18) for monitoring a variety of conditions of the inhaler. For example, the monitoring system can monitor a remaining power capacity of the power source 19 in order to provide an indication to the patient or user that the power capacity of the power source may be diminished to the point that the heating or cooling of the medicament may not continue for much longer without recharging the power source. The monitoring system can be of a variety of types known to those skilled in the art, and can include components that monitor the remaining charge on the power source, the level of medicament remaining in the reservoir, the temperature of the medicament in the reservoir, the temperature of the walls of the reservoir, the ambient temperature about the inhaler, etc.

As shown in FIG. 1, the monitoring system can include a signaling device 42 that can signal or indicate to the patient or user when a particular condition is detected in the inhaler. For example, in the event the monitoring system detects that the battery level has decreased below a threshold value, the signaling device can signal the patient or user, who can then locate an external power source to recharge the internal power source 19. Similarly, in the event the monitoring system detects that the remaining medicament level is below a threshold value, the signaling device can signal the patient or user, who can then replace or refill the medicament reservoir 12.

The signaling device 42 can be of a variety of types known to those skilled in the art, including audio and visual signaling types. The signal generated by the signaling device can be a binary function, e.g., either on or off, or can vary to indicate to the patient a variety of conditions. For example, a series of tones emitted by the signaling device can indicate to the patient that the battery level is low, while a series of different tones, or tones with a different pitch, can indicate to the patient that the medicament level is low.

The control system 18 can utilize a processor to increase the effectiveness and sophistication of the signaling system. For example, an external thermocouple 44 can detect an ambient, external temperature about the inhaler 10 to provide information that can be used by the processor to estimate a level of battery life remaining in the power source 19 based on this condition. To illustrate, when an external temperature about the inhaler is very near the desired temperature range for the medicament, the thermal source 16 may use very little power to maintain the medicament at the desired temperature, and an estimated battery life may be relatively long. In contrast, when the external temperature about the inhaler is very different than the desired temperature range for the medicament, the thermal source may have to utilize a great deal of power to maintain the medicament in the desired temperature range. The control system can account for this fact and can provide an earlier warning, via the signaling device, in the event a great deal of battery power may need to be expended to maintain the medicament in the desired temperature range.

In one aspect of the invention, the inhaler can include means for storing a medicament on or in the inhaler 10. The means for storing a medicament can include, without limitation, a vial or cartridge inserted into the inhaler, or a refillable vial or cartridge coupled within the inhaler. The inhaler can also include means for ejecting the medicament from the inhaler to deliver the medicament to a patient. The means for ejecting the medicament from the inhaler can include, without limitation, a depressable actuator formed within the inhaler reservoir that serves to expel medicament from the reservoir via propulsion by compressed gas. The inhaler can also include means for affecting a temperature of the medicament, which can include a thermoelectric heating or cooling device, and/or a combustion driven heating or cooling device.

In one aspect of the invention, a method for maintaining a medicament within a predetermined temperature range while the medicament is operably associated with an inhaler is also provided. The method, shown graphically at FIG. 3, can include the step 50 of disposing a quantity of the medicament within a reservoir associated with the inhaler and affecting 52 a temperature of the medicament with a thermal source. A temperature of the medicament can be monitored at 54 and the thermal source can be controlled at 56 by determining if the temperature of the medicament is outside of a predetermined temperature range. If the temperature is outside of the predetermined range, the process can repeat the step 52 of affecting the temperature of the medicament. The process can also include the step of monitoring at 58 a remaining power capacity of the power source. If the power capacity is below a threshold value, as determined in step 60, a signal can be generated at 61 to alert the patient or user of this condition. The process can also include the step of monitoring at 62 a remaining medicament level in the medicament reservoir. If the remaining medicament level is below the threshold, as determined in step 64, a signal can be generated at step 61 to the patient or user.

Figure 3:
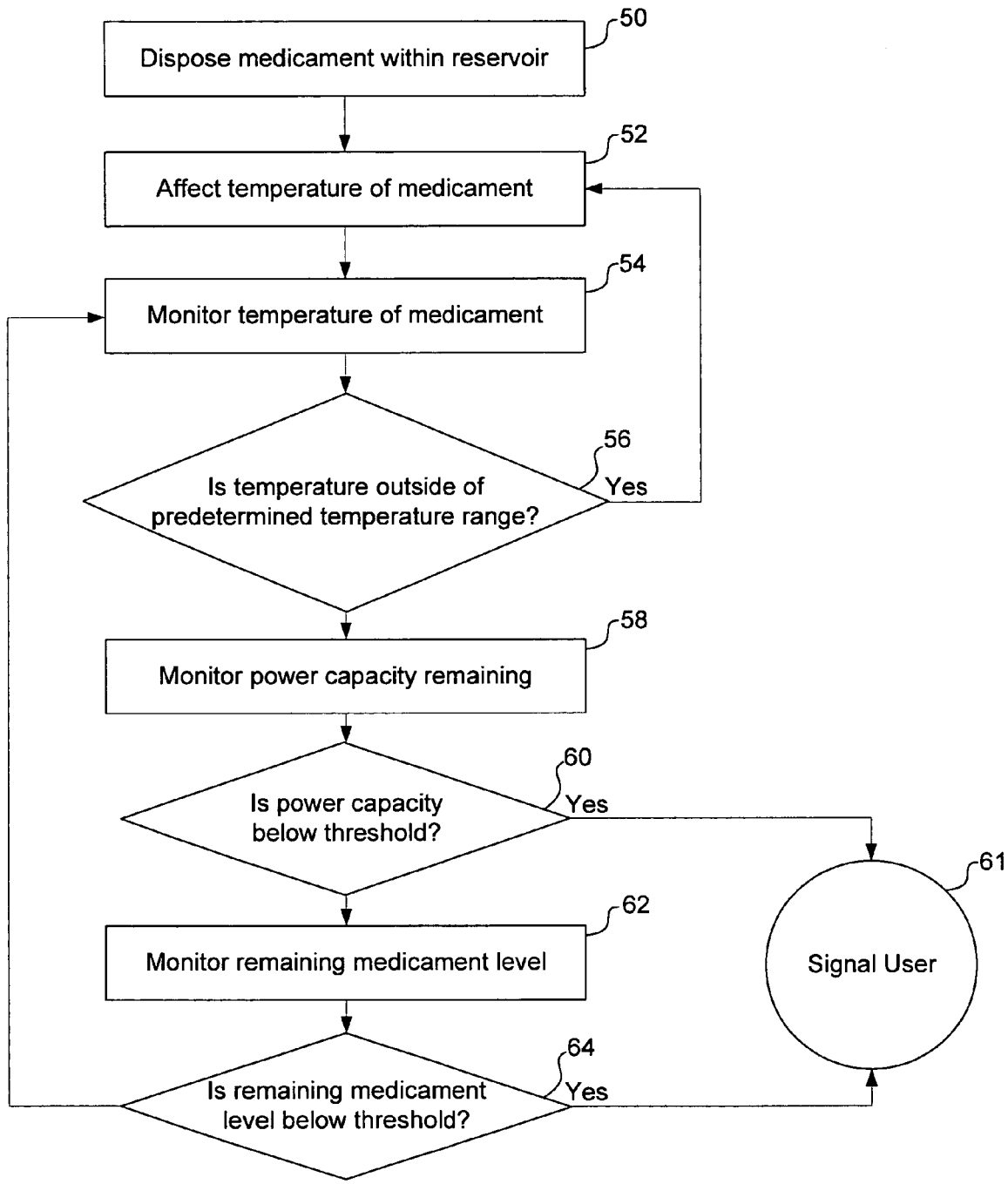
FIG. 3 is a flow chart illustrating an exemplary process of an embodiment of the present invention.

The process can be repeated as necessary to ensure the inhaler can be carried and used by the patient without resulting in the medicament experiencing temperatures outside the recommended storage temperatures. As the present inhaler is fully portable, the system can effectively maintain a medicament within a recommended temperature range while the patient or user goes about his or her normal daily activities. The specific steps shown in FIG. 3 are exemplary only, and can be modified in steps, order of steps, or the like without departing from embodiments of the present invention.

It is to be understood that the above-referenced arrangements are illustrative of the application for the principles of the present invention. Numerous modifications and alternative arrangements can be devised without departing from the spirit and scope of the present invention while the present invention has been shown in the drawings and described above in connection with the exemplary embodiments(s) of the invention. It will be apparent to those of ordinary skill in the art that numerous modifications can be made without departing from the principles and concepts of the invention as set forth in the claims.

What is claimed is:

1. A portable inhaler operable to control a temperature of a medicament of the inhaler, comprising:
   (a) a medicament reservoir being configured to store a medicament therein;
   (b) a medicament ejector operably coupled to the medicament reservoir and being configured to eject the medicament from the reservoir to deliver the medicament to a patient;
   (c) a controllable thermal source in thermal communication with at least an inside portion of the medicament reservoir and being configured to controllably maintain the medicament within a predetermined temperature range in a use-ready state by alternately heating and cooling at least the inside portion of the medicament reservoir; and
   (d) a thermal control system, in operable communication with the controllable thermal source, the thermal control system being configured to control the controllable thermal source to maintain the medicament within the predetermined temperature range.

2. The inhaler of claim 1, further comprising a power source coupled to the inhaler and operably coupled to the controllable thermal source to power the controllable thermal source.

3. The inhaler of claim 2, wherein the power source is a chargeable power source associated with a charging system operable to restore a charge to the power source.

4. The inhaler of claim 2, further comprising a monitoring system associated with the power source for monitoring a remaining power capacity of the power source.

5. The inhaler of claim 4, further comprising a signaling system associated with the monitoring system for signaling the patient when the remaining power capacity of the power source falls below a predetermined level.

6. The inhaler of claim 1, further comprising a monitoring system associated with the medicament reservoir for monitoring a remaining amount of the medicament in the reservoir.

7. The inhaler of claim 6, further comprising a signaling system associated with the monitoring system for signaling the patient when the remaining amount of the medicament falls below a predetermined level.

8. The inhaler of claim 1, further comprising control circuitry associated with the inhaler, the control circuitry being configured to allow customization of the inhaler, the customization of the inhaler selected from a patient's prescribed dosage, a type of medicament, a type of environment to which the inhaler is to be exposed, and combinations thereof.

9. The inhaler of claim 1, wherein the controllable thermal source is a cooling source.

10. The inhaler of claim 1, wherein the thermal control system is an electrical thermal control system.

11. The inhaler of claim 1, further comprising a housing operable for self-contained hand-held manipulation, the housing surrounding the medicament reservoir, the controllable thermal source, and the thermal control system.

12. A portable inhaler operable to control a temperature of a medicament stored on or in the inhaler, comprising:
   (a) means for storing a medicament on or in the inhaler;
   (b) means for ejecting the medicament from the inhaler to deliver the medicament to a patient;
   (c) means for affecting a temperature of the medicament, the means for affecting the temperature of the medicament being configured to controllably maintain the medicament within a predetermined temperature range in a use-ready state by alternately heating and cooling at least an inside portion of the means for storing the medicament; and
   (d) means for controlling the means for affecting the temperature of the medicament to enable control of the temperature of the medicament within the predetermined temperature range.

13. The inhaler of claim 12, further comprising a power source operably coupled to the inhaler to power the means for affecting the temperature of the medicament.

14. The inhaler of claim 13, further comprising a monitoring system associated with the power source for monitoring a remaining power capacity of the power source.

15. The inhaler of claim 14, further comprising a signaling system associated with the monitoring means for signaling the patient when the remaining power capacity of the power source falls below a predetermined level.

16. The inhaler of claim 13, wherein the power source is a chargeable power source associated a charging system operable to restore a charge to the power source.

17. The inhaler of claim 12, further comprising a monitoring system associated with the means for storing the fluid medicament for monitoring a remaining amount of the medicament.

18. The inhaler of claim 17, further comprising a signaling system associated with the monitoring system for signaling the patient when the remaining amount of the medicament falls below a predetermined level.

19. The inhaler of claim 12, further comprising control circuitry associated with the inhaler, the control circuitry being configured to allow customization of the inhaler, the customization of the inhaler selected from a patient's prescribed dosage, a type of medicament, a type of environment to which the inhaler is to be exposed, and combinations thereof.

20. The inhaler of claim 12, wherein the means for affecting a temperature of the medicament comprises a cooling source.

21. A method for maintaining a medicament within a predetermined temperature range while the medicament is operably associated with a portable inhaler, including the steps of:
 (a) disposing a quantity of the medicament within a reservoir associated with the portable inhaler;
 (b) affecting a temperature of the medicament with a thermal source, the thermal source being configured to controllably maintain the medicament within the predetermined temperature range in a use-ready state by alternately heating and cooling at least an inside portion of the medicament reservoir, thus helping to achieve an expected shelf-life of the medicament stored in the medicament reservoir until ejected from the reservoir;
 (c) monitoring a temperature of the medicament; and
 (d) controlling the thermal source to maintain the medicament within the predetermined temperature range.

22. The method of claim 21, comprising the further step of providing power to the thermal source with a power source coupled to the inhaler.

23. The method of claim 22, comprising the further steps of:
 monitoring a power capacity of the power source; and
 signaling a user of the inhaler when the power capacity of the power source falls below a predetermined level.

24. The method of claim 22, wherein the power source is a chargeable power source and further comprising a charging system associated with the power source, the charging system being operable to restore a charge to the power source.

25. The method of claim 21, comprising the further steps of:
 monitoring a remaining level of medicament within the reservoir; and
 signaling a user of the inhaler when the remaining level of medicament falls below a predetermined level.

26. The method of claim 21, further comprising control circuitry associated with the inhaler, the control circuitry being configured to allow customization of the inhaler, the customization of the inhaler selected from a patient's prescribed dosage, a type of medicament, a type of environment to which the inhaler is to be exposed, and combinations thereof.

27. The method of claim 21, wherein the step of affecting a temperature of the medicament includes the step of cooling the medicament.

* * * * *